(12) United States Patent
McLaughlin et al.

(10) Patent No.: US 12,310,794 B2
(45) Date of Patent: *May 27, 2025

(54) ULTRASONIC CHARACTERIZATION OF NON-LINEAR PROPERTIES OF TISSUE

(71) Applicant: Shenzhen Mindray Bio-Medical Electronics Co., Ltd., Shenzhen (CN)

(72) Inventors: Glen W. McLaughlin, San Carlos, CA (US); Albert Gee, Los Altos, CA (US)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/132,335

(22) Filed: Apr. 7, 2023

(65) Prior Publication Data

US 2023/0240662 A1 Aug. 3, 2023

Related U.S. Application Data

(63) Continuation of application No. 16/814,912, filed on Mar. 10, 2020, now Pat. No. 11,638,574.

(Continued)

(51) Int. Cl.
*A61B 8/08* (2006.01)
*A61B 8/00* (2006.01)

(52) U.S. Cl.
CPC .......... *A61B 8/5223* (2013.01); *A61B 8/0825* (2013.01); *A61B 8/085* (2013.01); *A61B 8/483* (2013.01)

(58) Field of Classification Search
CPC ..... A61B 8/5223; A61B 8/0825; A61B 8/085; A61B 8/483; A61B 8/54; A61B 8/5207;

(Continued)

(56) References Cited

U.S. PATENT DOCUMENTS

| 2002/0028994 A1* | 3/2002 | Kamiyama | A61B 8/463 600/437 |
| 2003/0060712 A1 | 3/2003 | Kawagishi et al. | |

(Continued)

FOREIGN PATENT DOCUMENTS

| CN | 107205722 A | 9/2017 | |
| CN | 109044407 A | 12/2018 | |
| WO | WO-2010004333 A1 * | 1/2010 | ........... G01S 15/895 |

OTHER PUBLICATIONS

Harput, Sevan (2012) "Use of chirps in medical ultrasound imaging" PhD thesis, University of Leeds, pp. 1-217 (Year: 2012).*

(Continued)

*Primary Examiner* — Anne M Kozak
*Assistant Examiner* — Kaitlyn E Sebastian
(74) *Attorney, Agent, or Firm* — Kory D. Christensen (57) ABSTRACT

Systems and methods for performing diagnostic sonography. Ultrasound information of a subject region can be collected. The ultrasound information can be based on one or more exponentially swept ultrasound chirp pulses transmitted toward the subject region and backscatter of the subject region from the one or more exponentially swept ultrasound chirp pulses. One or more corresponding harmonic responses and a corresponding fundamental response for each of the one or more exponentially swept ultrasound chirp pulses can be separated from the ultrasound information. Further, one or more non-linear properties of the subject region can be identified based on either or both of the one or more corresponding harmonic responses and the corresponding fundamental response for each of the one or more exponentially swept ultrasound chirp pulses.

22 Claims, 9 Drawing Sheets

Related U.S. Application Data (60) Provisional application No. 62/832,388, filed on Apr. 11, 2019.

(58) Field of Classification Search
CPC ....... A61B 8/44; A61B 8/5215; G01S 7/5202; G01S 7/52026; G01S 7/52038; G01S 15/895
See application file for complete search history.

(56) References Cited

U.S. PATENT DOCUMENTS

| | | | |
|---|---|---|---|
| 2003/0212326 A1* | 11/2003 | Ebbini | G01S 7/52038 600/458 |
| 2004/0059225 A1 | 3/2004 | Hao et al. | |
| 2016/0350573 A1* | 12/2016 | Kitchens, II | G06F 18/251 |
| 2019/0105018 A1 | 4/2019 | Okano et al. | |

OTHER PUBLICATIONS

Qin, Y. et al., "Optimizing frequency and pulse shape for ultrasound current source density imaging," IEEE Transactions on Ultrasonics, Ferroelectrics, and Frequency Control, 2012, pp. 2149-2155.

Harput, S., "Use of chirps in medical ultrasound imaging," PHD Thesis, University of Leeds, 2012.

Park, J. et al., "Combined chirp coded tissue harmonic and fundamental ultrasound imaging for intravascular ultrasound: 20-60MHz phantom and ex vivo results," Ultrasonics, vol. 53, Issue 2, 2013, pp. 369-376.

\* cited by examiner

ULTRASONIC CHARACTERIZATION OF NON-LINEAR PROPERTIES OF TISSUE

CROSS-REFERENCE TO RELATED APPLICATIONS

This application is a continuation of U.S. application Ser. No. 16/814,912, filed Mar. 10, 2020, for ULTRASONIC CHARACTERIZATION OF NON-LINEAR PROPERTIES OF TISSUE, with inventors Glen W. McLaughlin and Albert Gee, which claims priority to U.S. Provisional Patent Application No. 62/832,388, filed Apr. 11, 2019, for ULTRASONIC TISSUE CHARACTERIZATION OF THE B/A COEFFICIENT, the entire disclosures of which are hereby incorporated herein by reference.

TECHNICAL FIELD

The present disclosure relates to diagnostic sonography and more particularly to identifying non-linear properties of tissue through exponentially swept ultrasound chirp pulses.

BACKGROUND OF THE INVENTION

Ultrasound imaging is widely used for examining a wide range of materials and objects across a wide array of different applications. Ultrasound imaging provides a fast and easy tool for analyzing materials and objects in a non-invasive manner. As a result, ultrasound imaging is especially common in the practice of medicine as an ailment diagnosis, treatment, and prevention tool. Specifically, because of its relatively non-invasive nature, low cost and fast response time ultrasound imaging is widely used throughout the medical industry to diagnose and prevent ailments. Further, as ultrasound imaging is based on non-ionizing radiation it does not carry the same risks as other diagnosis imaging tools, such as X-ray imaging or other types of imaging systems that use ionizing radiation.

Characterization of tissue properties, and in particular in-vivo tissue properties, with ultrasound has been a long-standing area of research for the past several decades. Specifically, efforts have been undertaken to efficiently gather and interpret ultrasound measurements for characterizing both bulk tissue properties and regional tissue properties. However, extracting meaningful and consistent ultrasound measurements and interpreting these ultrasound measurements to identify tissue properties has been challenging endeavor for numerous reasons.

SUMMARY

According to various embodiments, a method for performing diagnostic sonography includes collecting ultrasound information of a subject region. The ultrasound information can be based on one or more exponentially swept ultrasound chirp pulses transmitted toward the subject region and backscatter of the subject region from the one or more exponentially swept ultrasound chirp pulses. The method can also include separating one or more corresponding harmonic responses and a corresponding fundamental response for each of the one or more exponentially swept ultrasound chirp pulses from the ultrasound information. Further, the method can include identifying one or more non-linear properties of the subject region based on either or both of the one or more corresponding harmonic responses and the corresponding fundamental response for each of the one or more exponentially swept ultrasound chirp pulses.

In certain embodiments, a system for performing diagnostic sonography includes an ultrasound transducer and a main processing console. The ultrasound transducer can collect ultrasound information of a subject region. The ultrasound information can be based on one or more exponentially swept ultrasound chirp pulses transmitted toward the subject region and backscatter of the subject region from the one or more exponentially swept ultrasound chirp pulses. The main processing console can separate one or more corresponding harmonic responses and a corresponding fundamental response for each of the one or more exponentially swept ultrasound chirp pulses from the ultrasound information. The main processing console can also identify one or more non-linear properties of the subject region based on either or both of the one or more corresponding harmonic responses and the corresponding fundamental response for each of the one or more exponentially swept ultrasound chirp pulses.

In various embodiments, a system for performing diagnostic sonography includes one or more processors and a computer-readable medium providing instructions accessible to the one or more processors to cause the one or more processors to collect ultrasound information of a subject region. The ultrasound information can be based on one or more exponentially swept ultrasound chirp pulses transmitted toward the subject region and backscatter of the subject region from the one or more exponentially swept ultrasound chirp pulses. The instructions can further cause the one or more processors to separate one or more corresponding harmonic responses and a corresponding fundamental response for each of the one or more exponentially swept ultrasound chirp pulses from the ultrasound information. Additionally, the instructions can cause the one or more processors to identify one or more non-linear properties of the subject region based on either or both of the one or more corresponding harmonic responses and the corresponding fundamental response for each of the one or more exponentially swept ultrasound chirp pulses.

DETAILED DESCRIPTION

Characterization of tissue properties, and in particular in-vivo tissue properties, with ultrasound has been a long-standing area of research for the past several decades. Specifically, efforts have been undertaken to efficiently gather and interpret ultrasound measurements for characterizing both bulk tissue properties and regional tissue properties. However, extracting meaningful and consistent ultrasound measurements and interpreting these ultrasound measurements to identify tissue properties has been challenging endeavor for numerous reasons. First, basic ultrasound measurements tend to be operator dependent making it difficult to consistently and accurately identify tissue characteristics from measurements gathered across different operators. Additionally, ultrasound measurements are prone to noise making it difficult to accurately identify tissue characteristics from the measurements. Further, ultrasound can have difficulties penetrating areas of interest at great depths making it difficult to gather measurements for accurately identifying tissue characteristics of the areas of interest. Additionally, correlation across different ultrasound system implementations is challenging, thereby leading to consistency and accuracy issues associated with characterizing tissue from measurements gathered across the different system implementations.

With respect to in-vivo tissue properties, movement of the tissue creates problems in gathering meaningful ultrasound measurements and accurately identifying tissue characteristics from the measurements. As a result, measurements for identifying tissue characteristics, e.g. non-linear tissue characteristics, are typically made through excised tissue. However, the process of surgically removing a patient's tissue complicates the overall process of tissue characterization and presents numerous risks for the patient.

The following disclosure describes systems, methods, and computer-readable media for solving these problems/discrepancies. Specifically, the present technology involves system, methods, and computer-readable media for identifying non-linear properties of a subject region through one or more exponentially swept ultrasound chirp pulses transmitted towards the subject region. More specifically, the present technology involves systems, methods, and computer-readable media for identifying non-linear properties of the subject region based on either or both one or more corresponding harmonic responses and a corresponding fundamental response for each of the one or more exponentially swept ultrasound chirp pulses.

Reference is now made to the figures, where like components are designated by like reference numerals throughout the disclosure. Some of the infrastructure that can be used with embodiments disclosed herein is already available, such as general-purpose computers, computer programming tools and techniques, digital storage media, and communications networks. A computing device may include a processor such as a microprocessor, microcontroller, logic circuitry, or the like. The processor may include a special purpose processing device such as an Application Specific Integrated Circuit (ASIC), a Programmable Array Logic (PAL), a Programmable Logic Array (PLA), a Programmable Logic Device (PLD), a Field Programmable Gate Array (FPGA), or other customized or programmable devices. The computing device may also include a computer-readable storage device such as a non-volatile memory, a static Random Access Memory (RAM), a dynamic RAM, a Read-Only Memory (ROM), a Compact Disc Read-Only Memory (CD-ROM), a disk, a tape, a magnetic, optical, flash memory, or other non-transitory computer-readable storage mediums.

Various aspects of certain embodiments may be implemented using hardware, software, firmware, or a combination thereof. As used herein, a software module or component may include any type of computer instruction or computer executable code located within or on a computer-readable storage medium. A software module may, for instance, comprise one or more physical or logical blocks of computer instructions, which may be organized as a routine, program, object, component, data structure, etc., which performs one or more tasks or implements particular abstract data types.

In certain embodiments, a particular software module may comprise disparate instructions stored in different locations of a computer-readable storage medium, which together implement the described functionality of the module. Indeed, a module may comprise a single instruction or many instructions, and may be distributed over several different code segments, among different programs, and across several computer-readable storage media. Some embodiments may be practiced in a distributed computing environment where tasks are performed by a remote processing device linked through a communications network.

The embodiments of the disclosure will be best understood by reference to the drawings. The components of the disclosed embodiments, as generally described and illustrated in the figures herein, could be arranged and designed in a wide variety of different configurations. Furthermore, the features, structures, and operations associated with one embodiment may be applicable to or combined with the features, structures, or operations described in conjunction with another embodiment. In other instances, well-known structures, materials, or operations are not shown or described in detail to avoid obscuring aspects of this disclosure.

Thus, the following detailed description of the embodiments of the systems and methods of the disclosure is not intended to limit the scope of the disclosure, as claimed, but is merely representative of possible embodiments. In addition, the steps of a method do not necessarily need to be executed in any specific order, or even sequentially, nor need the steps be executed only once.

Figure 1:
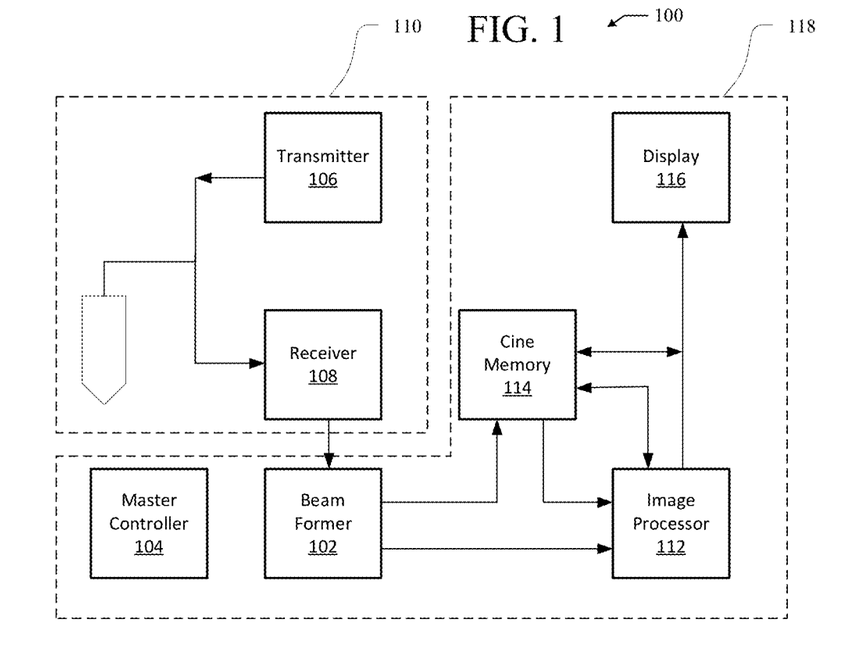
FIG. 1 illustrates an example of an ultrasound system.

FIG. 1 is a schematic block diagram of one exemplary embodiment of a medical imaging device, such as an ultrasound imaging device 100. Those skilled in the art will recognize that the principles disclosed herein may be applied to a variety of medical imaging devices, including, without limitation, an X-ray imaging device, a computed tomography (CT) imaging device, a magnetic resonance imaging (MRI) device, and a positron-emission tomography (PET) imaging device. As such, the components of each device may vary from what is illustrated in FIG. 1.

In one embodiment, the ultrasound imaging device 100 may include an array focusing unit, referred to herein as a beam former 102, by which image formation can be performed on a scanline-by-scanline basis. The device may be controlled by a master controller 104, implemented by a microprocessor or the like, which accepts operator inputs through an operator interface and in turn controls the various subsystems of the device 100.

For each scanline, a transmitter 106 generates a radio-frequency (RF) excitation voltage pulse waveform and applies it with appropriate timing across a transmit aperture (defined, in one embodiment, by a sub-array of active elements) to generate a focused acoustic beam along the scanline.

RF echoes received by one or more receive apertures or receiver 108 are amplified, filtered, and then fed into the beam former 102, which may perform dynamic receive focusing, i.e., realignment of the RF signals that originate from the same locations along various scan lines. Collectively, the transmitter 106 and receiver 108 may be components of a transducer 110. Various types of transducers 110 are known in the ultrasound imaging art, such as linear probes, curvilinear probes, and phased array probes.

An image processor 112 may perform processing tasks specific to various active imaging mode(s) including 2D scan conversion that transforms the image data from an acoustic line grid into an X-Y pixel image for display. For other modes, such as a spectral Doppler mode, the image processor 112 may perform wall filtering followed by spectral analysis of Doppler-shifted signal samples using typically a sliding Fast Fourier Transform-window (FFT-window). The image processor 112 may also generate a stereo audio signal output corresponding to forward and reverse flow signals. In cooperation with the master controller 104, the image processor 112 may also format images from two or more active imaging modes, including display annotation, graphics overlays and replay of cine loops and recorded timeline data.

A cine memory 114 provides resident digital image storage to enable single image or multiple image loop review, and acts as a buffer for transfer of images to digital archival devices, such as hard disk drives or optical storage. In some systems, the video images at the end of the data processing path may be stored to the cine memory. In state-of-the-art systems, amplitude-detected, beamformed data may also be stored in cine memory 114. For spectral Doppler mode, wall-filtered, baseband Doppler I/Q data for a user-selected range gate may be stored in cine memory 114. Subsequently, a display 116, such as a computer monitor, may display ultrasound images created by the image processor 112 and/or images using data stored in the cine memory 114.

The beam former 102, the master controller 104, the image processor 112, the cine memory 114, and the display 116 can be included as part of a main processing console 118 of the ultrasound imaging device 100, which may include more or fewer components or subsystems than are illustrated. The ultrasound transducer 110 may be incorporated into an apparatus that is separate from the main processing console 118, e.g. in a separate apparatus that is wired or wirelessly connected to the main processing console 118. This allows for easier manipulation of the ultrasound transducer 110 when performing specific ultrasound procedures on a patient. Further, the transducer 110 can be an array transducer that includes an array of transmitting and receiving elements for transmitting and receiving ultrasound waves.

Those skilled in the art will recognize that a wide variety of ultrasound imaging devices are available on the market, and additional details relating to how images are generated is unnecessary for a thorough understanding of the principles disclosed herein. Specifically, the systems, methods, and computer-readable media described herein can be applied through an applicable ultrasound imaging device of the wide variety of ultrasound imaging devices available on the market.

Exponentially swept ultrasound chirps can be applied to characterize non-linearity of a subject region. Specifically, exponentially swept ultrasound chirps can be applied to identify non-linear properties of tissue. More specifically, exponentially swept ultrasound chirps can be applied to identify non-linear properties of in-vivo tissue. Characterizing tissue that remains in-vivo is advantageous as it reduces the complexity associated with surgically removing the tissue to ultimately characterize the tissue. Further, characterizing tissue that remains in-vivo is advantageous as it eliminates patient risks associated with the surgical procedure(s) of removing the tissue.

Non-linear properties of a subject region can include applicable non-linear properties of a subject region capable of being identified through ultrasound. Specifically, non-linear properties of a subject region can include applicable acoustic non-linear properties of tissue capable of being identified through ultrasound. For example, non-linear properties of a subject region can include values of an acoustic non-linearity parameter B/A for tissue.

Exponentially swept chirp pulses can be represented as Equations 1 and 2 shown below.

$$x(t) = e^{i2\pi \frac{f_1}{a}(e^{at}-1)} \quad \text{Equation 1}$$

$$\theta(f) = A(f \log(f) - f) - A(\log f_1 - T_{start})f \quad \text{Equation 2}$$

In equation 1, $$a = \frac{\ln\left(\frac{f_1}{f_2}\right)}{T}$$

and in equation 2, $$A = \frac{T}{\ln\frac{f_2}{f_1}} \cdot f_1$$

is the start frequency of the exponentially swept chirp pulse and $f_2$ is the stop frequency of the exponentially swept chirp pulse. T is the pulse duration of the exponentially swept chip pulse and $T_{start}$ is the pulse start time.

Exponentially swept chirp signals have the characteristic that the group delay between fundamental and harmonic responses to the chirp signals is a function of the $N^{th}$ order harmonic. More specifically, the group delay between the fundamental and harmonic responses to the chirp signals is not a function of the frequency of the harmonic responses, e.g. the instantaneous frequency of the chirp signals corresponding to the harmonic responses. Accordingly, the fundamental and the $N^{th}$ order harmonic responses for an exponentially swept chirp signal sum to form their own respective impulse responses offset by the difference in corresponding group delays between the corresponding harmonic responses and the corresponding fundamental response, what is otherwise referred to as the time delay between the corresponding harmonic responses and fundamental response.

These response characteristics of exponentially swept chirp signals are further illustrated by the following equations. Equation 3 is the instantaneous frequency of the exponentially swept chirp signal.

$$f_{instant}(t) = \frac{1}{2\pi} \frac{\partial \theta_{time}(t)}{\partial t} \quad \text{Equation 3}$$

Equation 4 is the production time for the fundamental response $\tau_{groupDelay}(f)$ of the exponentially swept chirp signal.

$$\tau_{groupDelay}(f) = -\frac{1}{2\pi} \frac{\partial \theta_{freq}(f)}{\partial f} \quad \text{Equation 4}$$

As follows, the production time for the fundamental response $\tau_{groupDelay}(f)$, as shown in Equation 5, can be represented as a function of the start frequency $f_1$ and the stop frequency $f_2$ of the exponentially swept chirp pulse.

$$\tau_{groupDelay}(f) = T \frac{\ln\left(\frac{f}{f_2}\right)}{\ln\left(\frac{f_2}{f_1}\right)} \quad \text{Equation 5}$$

Further, the production time for the $N^{th}$ order harmonic $\hat{\tau}_{groupDelay}(f)$ of the exponentially swept chirp signal can be represented as shown in Equation 6.

$$\hat{\tau}_{groupDelay}(f) = T \frac{\ln\left(\frac{f}{Nf_1}\right)}{\ln\left(\frac{f_2}{f_1}\right)} \quad \text{Equation 6}$$

Accordingly, the time delay $\Delta_t$ between the corresponding $N^{th}$ order harmonic responses and the fundamental response for the exponentially swept chirp signal can be expressed by Equation 7.

$$\Delta_t = \tau_{groupDelay}(f) - \hat{\tau}_{groupDelay}(f) = T \frac{\ln(N)}{\ln\left(\frac{f_2}{f_1}\right)} \quad \text{Equation 7}$$

As shown in Equation 7, $\Delta_t$ is a function of N but not a function of f, e.g. the instantaneous frequency of the chirp signal corresponding to the harmonic responses. Therefore, across frequency, all $N^{th}$ order harmonics have the same group delay and will thus sum to form a "harmonic" impulse response. Specifically, all frequencies arising from a particular harmonic order can arrive at the same time, creating a harmonic impulse response that is offset from a corresponding fundamental impulse response by the time delay $\Delta_t$.

As the harmonic responses for an $N^{th}$ order harmonic can be summed to effectively form a single harmonic impulse response, an exponentially swept ultrasound chirp pulse can effectively create two impulse responses, a fundamental response and a corresponding $N^{th}$ harmonic response. Specifically, backscatter from a subject region created in response to an exponentially swept ultrasound chirp pulse interacting with the subject region can include a fundamental response and one or more harmonic responses, e.g. corresponding to each N harmonic. These responses, as shown in Equation 7, are displaced in time by the time delay $\Delta_t$. This time delay can be a known amount, e.g. based on N and the start and stop frequencies $f_1$ and $f_2$ of the exponentially swept ultrasound chirp pulse.

This time delay between the harmonic response(s) and the fundamental response to the exponentially swept chirp can be dependent on the presence of non-linearity in the subject region. Specifically, this time delay between the fundamental response and the harmonic response(s) can be created when the subject region interacting with the exponentially swept chirp includes non-linearity. Conversely, when the subject region lacks non-linearity, then the created fundamental response and the harmonic response(s) can lack this time shift. In turn, the time delay created in response to non-linearity in the subject region can serve as a basis for identifying non-linear properties of the subject region. Specifically, the time delay between the fundamental response and the harmonic response(s) can form the basis for the superposition of two or more images created from the ultrasound backscatter. In turn, the amount of displacement present between the two or more superposition images, e.g. based at least in part on the time delay between the fundamental response and the harmonic response(s), can be analyzed to identify non-linear properties of the subject region.

Figure 2:
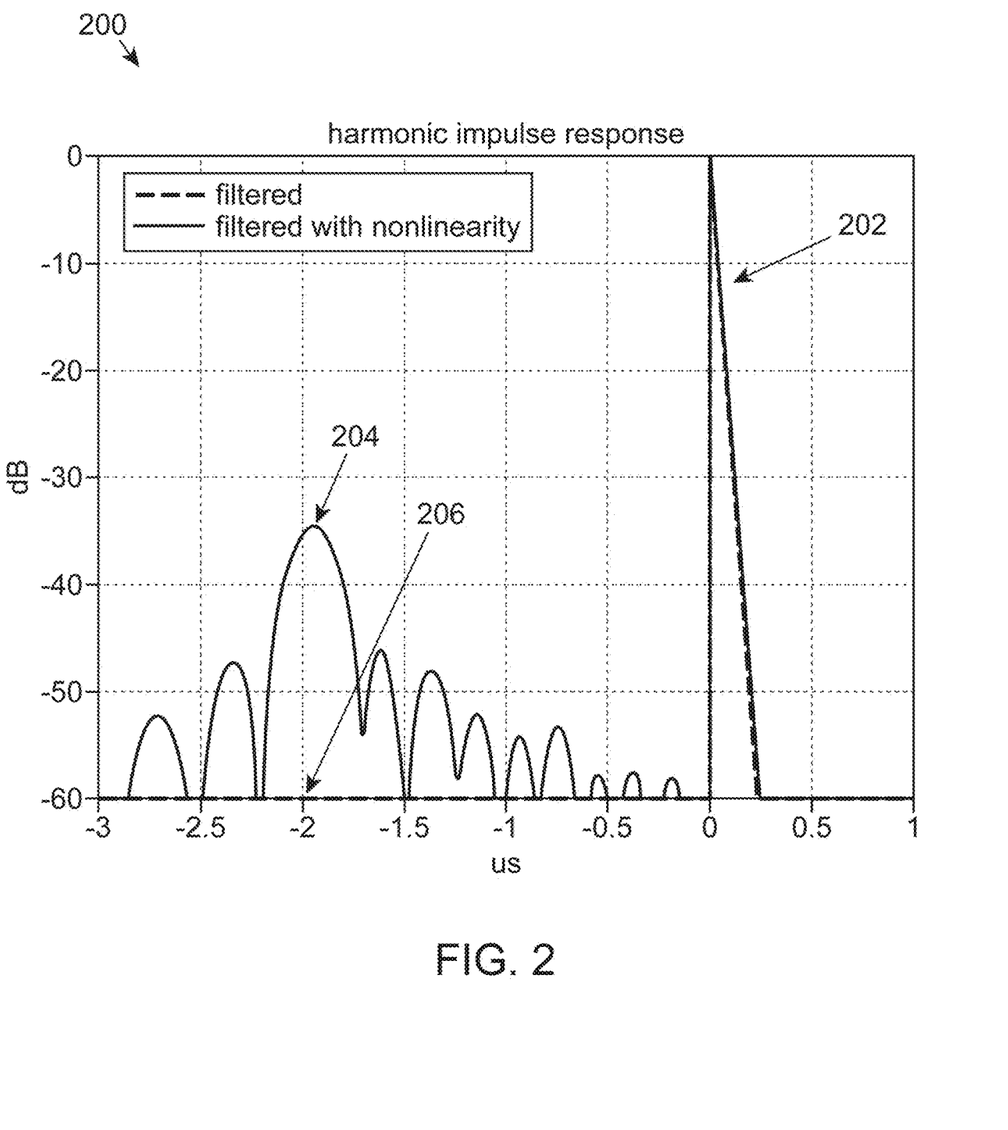
FIG. 2 is a plot of intensities of fundamental and harmonic responses to an exponentially swept ultrasound chirp pulse as a function of time for both linear and non-linear subject regions.

FIG. 2 shows the time offset between fundamental and harmonic responses that is created when the subject region has non-linearity. Specifically, FIG. 2 is a plot 200 of intensities of fundamental and harmonic responses to an exponentially swept ultrasound chirp pulse as a function of time for both linear and non-linear subject regions. As shown in FIG. 2, both the linear subject region and the non-linear subject region have a fundamental impulse response at time 0.0 uS, 202. Additionally, and as shown in FIG. 2, the non-linear subject region has a time shifted harmonic response 204 at time −2.0 uS, 206. However, the linear subject region does not show corresponding time shifted harmonic response(s), e.g. due to the lack of non-linearity of the linear subject region.

Figure 3A:
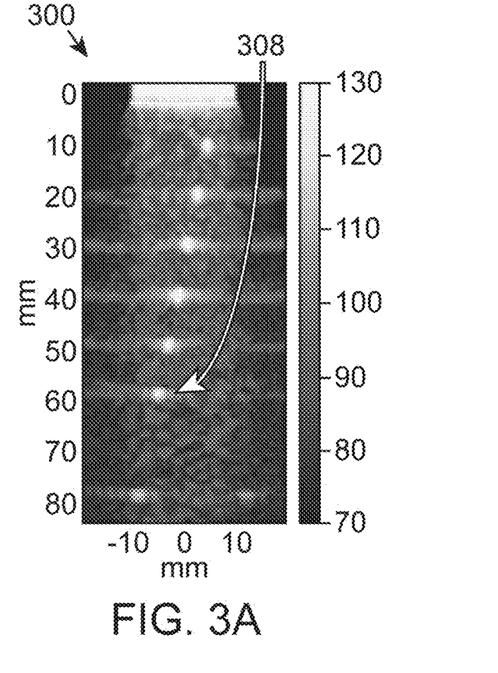
FIG. 3A is a positive phase image of a subject region created through a Gaussian ultrasound transmit profile.
Figure 3B:
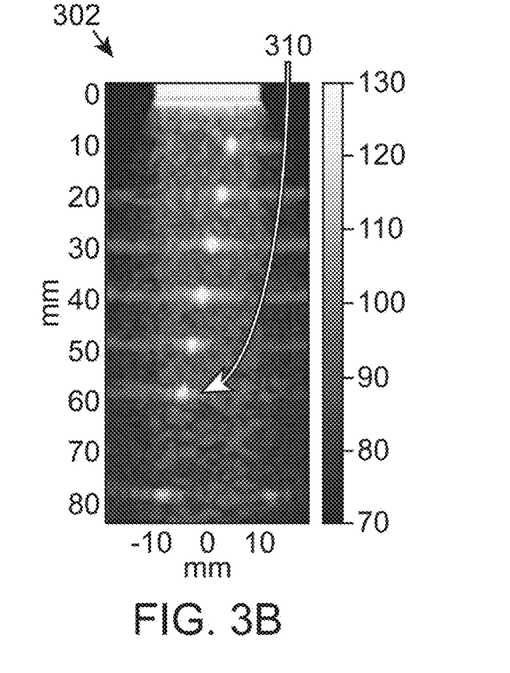
FIG. 3B is a negative phase image of the subject region created through the Gaussian ultrasound transmit profile.
Figure 3C:
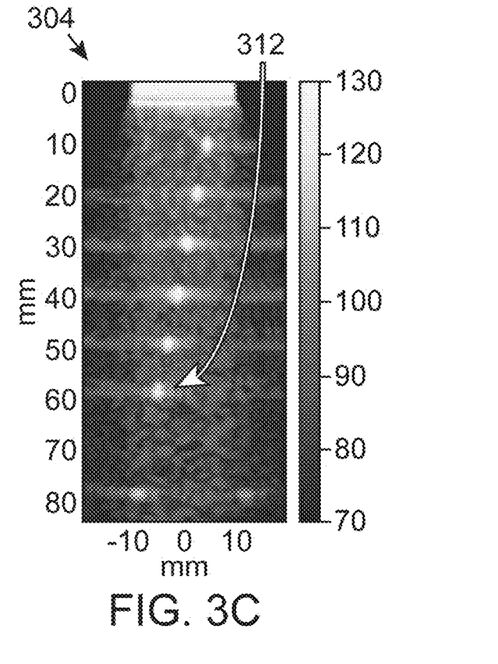
FIG. 3C is a sum image of the images shown in FIGS. 3A and 3B.
Figure 3D:
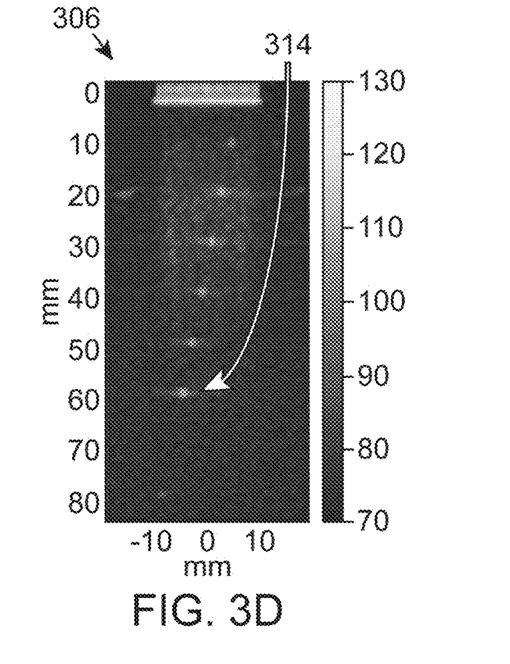
FIG. 3D is a difference image of the images shown in FIGS. 3A and 3B.

FIG. 3A is a positive phase image 300 of a subject region created through a Gaussian ultrasound transmit profile. FIG. 3B is a negative phase image 302 of the subject region created through the Gaussian ultrasound transmit profile. FIG. 3C is a sum image 304 of the images shown in FIGS. 3A and 3B. FIG. 3D is a difference image 306 of the images shown in FIGS. 3A and 3B.

The Gaussian ultrasound transmit profile is typically used in forming images through ultrasound. Specifically, phase inversion or a positive oriented pulse and a negative oriented pulse through a Gaussian ultrasound transmit profile used to generate two separate images through harmonic mode imaging. In turn, the fundamental component can cancel out when the two images are combined to leave only the harmonic component(s). The corresponding positive phase image 300 shown in FIG. 3A is created through a positive narrowband Gaussian transmit profile while the corresponding negative phase image 302 is created through a negative narrowband Gaussian transmit profile.

As shown in the positive and negative phase images 300 and 302, points in the imaging field are offset by 10 mm. For example, the positive phase image 300 has a point 308 at 60 mm that is offset from adjacent points, e.g. the point at 50 mm, by around 10 mm. The same can be seen in the negative phase image 302, where points, e.g. the point at 60 mm 310, are offset from adjacent points by around 10 mm. Further and as shown in the positive and negative phase images 300 and 302, the positive phase and negative phase images 300 and 302, the harmonic signal(s) are not offset from the fundamental signal(s). Specifically, corresponding harmonic signal(s) and fundamental signal(s) form single corresponding points, e.g. point 308, and not two separate points, as will be shown in greater detail later. This shows the lack of separation, e.g. due to time delay, that is created through application of a typical ultrasound transmit profile, e.g. a Gaussian ultrasound transmit profile.

This lack of separation between corresponding harmonic signal(s) and fundamental signal(s) is further illustrated in the sum image 304 and the difference image 306 shown in FIGS. 3C and 3D. The sum image 304 of the positive oriented pulse and the negative oriented pulse applied to create the corresponding positive and negative phase images 300 and 302 represents the fundamental signal(s). Further, the difference image 306 of the positive oriented pulse and the negative oriented pulse applied to create the corresponding positive and negative phase images 300 and 302 represents the harmonic signal(s). As shown, in the sum image 304, the fundamental signal at 60 mm is a single point 312. Similarly, in the difference image 306, the harmonic signal is also a single point 314 that is located at 60 mm. The points 312 and 314 are both at 60 mm and do not show a separation of depth corresponding to a lack of time delay between the fundamental and harmonic signals.

Figure 4A:
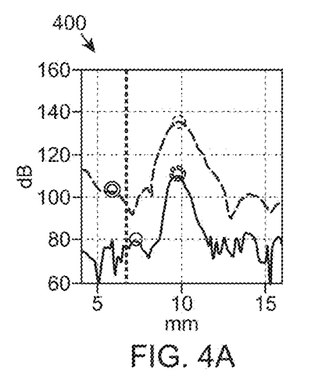
FIG. 4A is an intensity plot of fundamental and harmonic responses to a narrowband Gaussian transmit profile centered at a 10 mm depth.
Figure 4B:
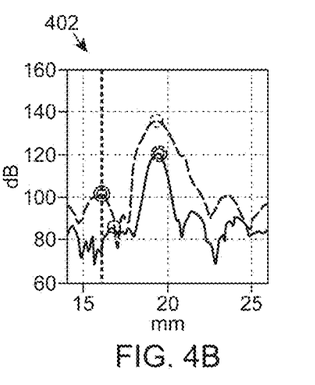
FIG. 4B is an intensity plot of the fundamental and harmonic responses to the narrowband Gaussian transmit profile centered at a 20 mm depth.
Figure 4C:
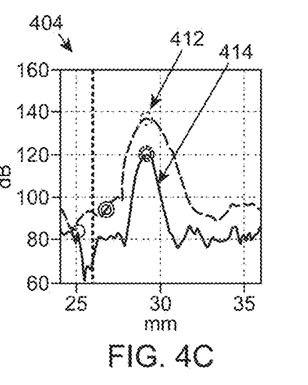
FIG. 4C is an intensity plot of the fundamental and harmonic responses to the narrowband Gaussian transmit profile centered at a 30 mm depth.
Figure 4D:
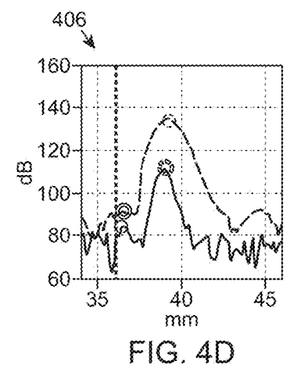
FIG. 4D is an intensity plot of the fundamental and harmonic responses to the narrowband Gaussian transmit profile centered at a 40 mm depth.
Figure 4E:
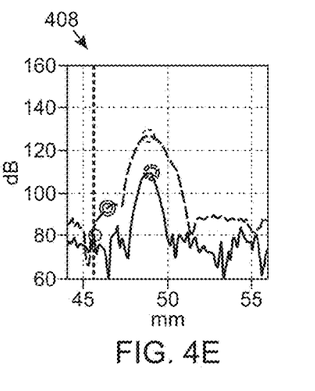
FIG. 4E is an intensity plot of the fundamental and harmonic responses to the narrowband Gaussian transmit profile centered at a 50 mm depth.
Figure 4F:
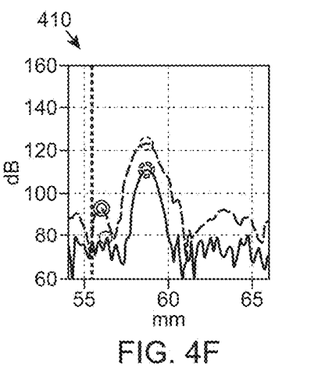
FIG. 4F is an intensity plot of the fundamental and harmonic responses to the narrowband Gaussian transmit profile centered at a 60 mm depth.

FIG. 4A is an intensity plot 400 of fundamental and harmonic responses to a narrowband Gaussian transmit profile centered at a 10 mm depth. FIG. 4B is an intensity plot 402 of the fundamental and harmonic responses to the narrowband Gaussian transmit profile centered at a 20 mm depth. FIG. 4C is an intensity plot 404 of the fundamental and harmonic responses to the narrowband Gaussian transmit profile centered at a 30 mm depth. FIG. 4D is an intensity plot 406 of the fundamental and harmonic responses to the narrowband Gaussian transmit profile centered at a 40 mm depth. FIG. 4E is an intensity plot 408 of the fundamental and harmonic responses to the narrowband Gaussian transmit profile centered at a 50 mm depth. FIG. 4F is an intensity plot 410 of the fundamental and harmonic responses to the narrowband Gaussian transmit profile centered at a 60 mm depth.

As can be seen in FIG. 4C, the response from the fundamental signal 412 and the response from the harmonic component 414 are both collocated in space at approximately 30 mm of depth. The same collocation of the fundamental and harmonic signal can bee see from the other intensity plots FIGS. 4A, 4B, 4D, 4E, and 4F. This further shows that a narrowband Gaussian transmit profile, that is the typical transmit used in ultrasound systems, does not produce an offset in distance between the fundamental and harmonic components.

Figure 5A:
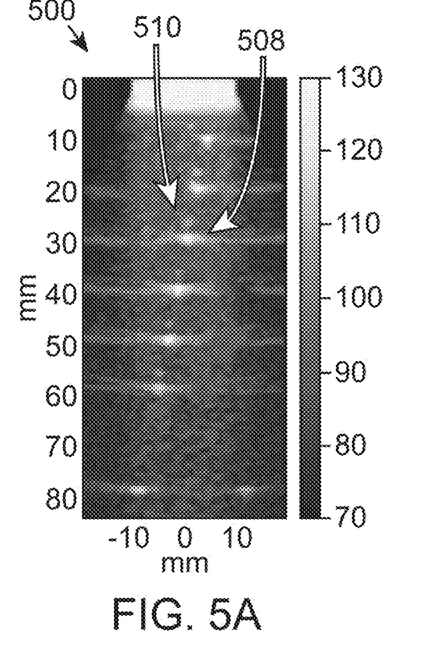
FIG. 5A is a positive phase image of a subject region created through an exponentially swept ultrasound chirp signal.
Figure 5B:
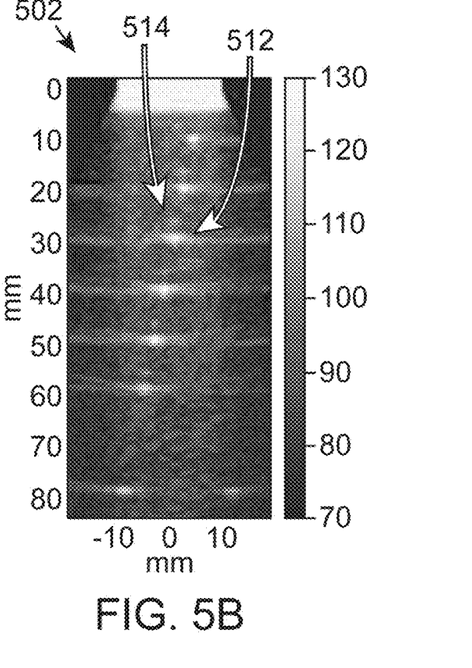
FIG. 5B is a negative phase image of the subject region created through the exponentially swept ultrasound chirp signal.
Figure 5C:
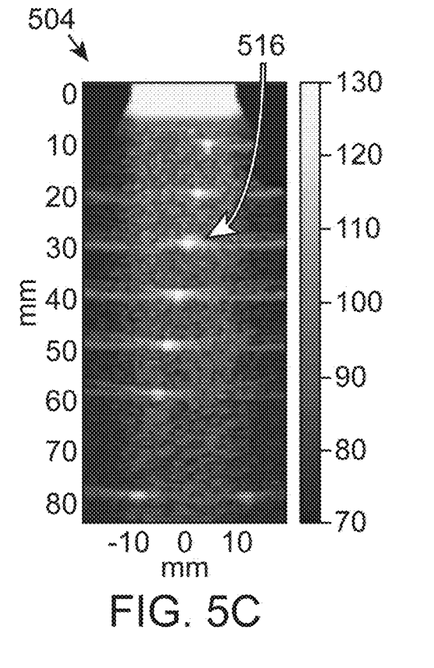
FIG. 5C is a sum image of the images shown in FIGS. 5A and 5B.
Figure 5D:
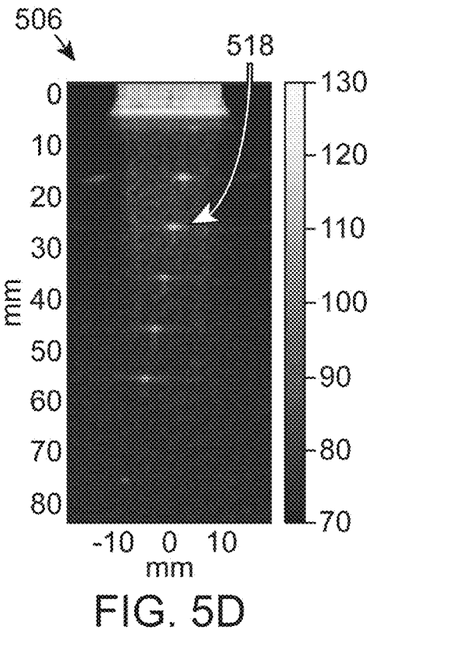
FIG. 5D is a difference image of the images shown in FIGS. 5A and 5B.

FIG. 5A is a positive phase image 500 of a subject region created through an exponentially swept ultrasound chirp signal. FIG. 5B is a negative phase image 502 of the subject region created through the exponentially swept ultrasound chirp signal. FIG. 5C is a sum image 504 of the images shown in FIGS. 5A and 5B. FIG. 5D is a difference image 506 of the images shown in FIGS. 5A and 5B.

FIGS. 5A-D show the time delay created between fundamental and harmonic responses to an exponentially swept ultrasound chirp signal. In the positive phase image 500, the fundamental signal is located at the point 508 at 30 mm. Further, the harmonic response in the positive phase image 500 is at point 510 before 30 mm, which is offset from the point 508 of the fundamental response at 30 mm. This offset corresponds to the time delay between the fundamental and harmonic responses created through application of the exponentially swept ultrasound chirp signal. This spatial offset is also shown in the negative phase image 502 where the fundamental response is located at point 512 at 30 mm, while the harmonic response is located at point 514, which is offset from the point 512 of the fundamental response at 512.

This time separation between corresponding harmonic signal(s) and fundamental signal(s) is further illustrated in the sum image 504 and the difference image 506 shown in FIGS. 5C and 5D. The sum image 504 of the positive oriented exponentially swept ultrasound chirp pulse and the negative oriented exponentially swept ultrasound chirp pulse, corresponding to FIGS. 5A and 5B, represents the fundamental signal(s). Further, the difference image 506 of the positive oriented exponentially swept ultrasound chirp pulse and the negative oriented exponentially swept ultrasound chirp pulse, corresponding to FIGS. 5A and 5B, represents the harmonic signal(s). As shown in FIG. 5C, there is a fundamental response at point 516 at 30 mm. Further and as shown in FIG. 5D, there a harmonic response at point 518. The harmonic response at point 518 is shifted from the fundamental response at point 516. Specifically, the fundamental response at point 516 is at 30 mm, while the harmonic response at point 518 is shifted closer to 26 mm. This spatial shift corresponds to the time shift between the fundamental response and the harmonic response to the exponentially swept ultrasound chirp pulses.

Figure 6A:
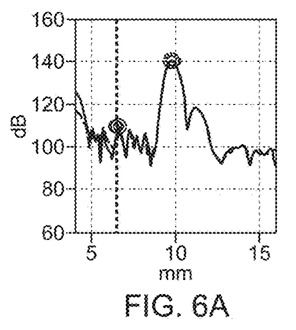
FIG. 6A is an intensity plot of fundamental and harmonic responses to an exponentially swept ultrasound chirp pulse centered at a 10 mm depth.
Figure 6B:
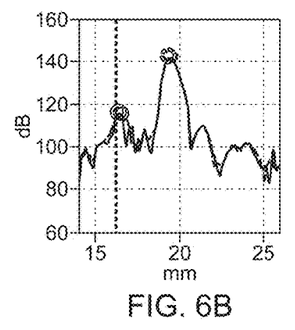
FIG. 6B is an intensity plot of the fundamental and harmonic responses to the exponentially swept ultrasound chirp pulse centered at a 20 mm depth.
Figure 6C:
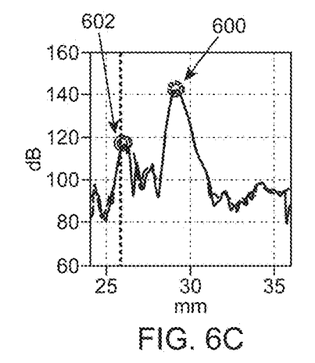
FIG. 6C is an intensity plot of the fundamental and harmonic responses to the exponentially swept ultrasound chirp pulse centered at a 30 mm depth.
Figure 6D:
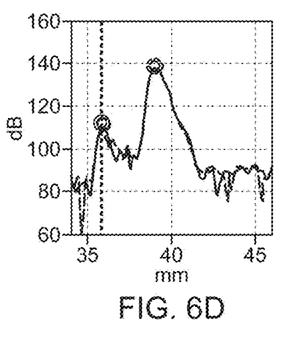
FIG. 6D is an intensity plot of the fundamental and harmonic responses to the exponentially swept ultrasound chirp pulse centered at a 40 mm depth.
Figure 6E:
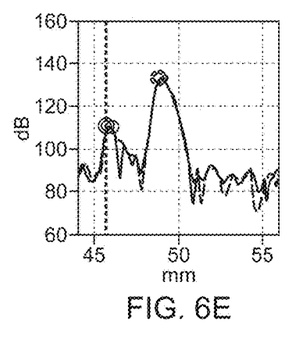
FIG. 6E is an intensity plot of the fundamental and harmonic responses to the exponentially swept ultrasound chirp pulse centered at a 50 mm depth.
Figure 6F:
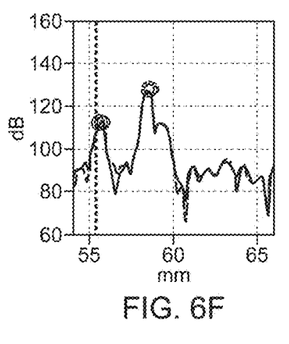
FIG. 6F is an intensity plot of the fundamental and harmonic responses to the exponentially swept ultrasound chirp pulse centered at a 60 mm depth.
Figure 7A:
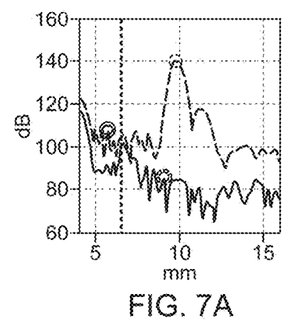
FIG. 7A is a plot of sums and differences of the fundamental and harmonic responses in FIG. 6A centered at a 10 mm depth.
Figure 7B:
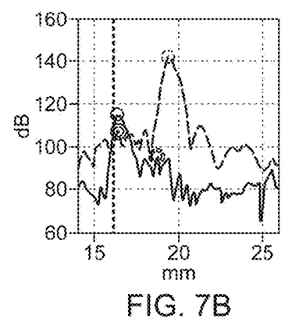
FIG. 7B is a plot of sums and differences of the fundamental and harmonic responses in FIG. 6B centered at a 20 mm depth.
Figure 7C:
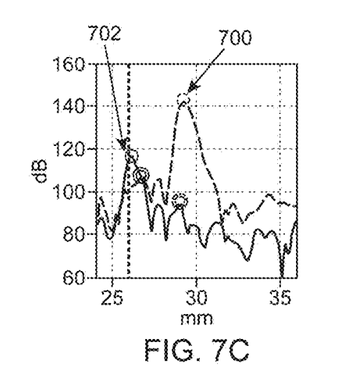
FIG. 7C is a plot of sums and differences of the fundamental and harmonic responses in FIG. 6C centered at a 30 mm depth.
Figure 7D:
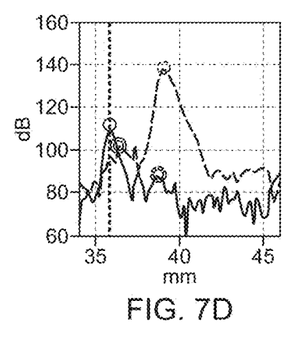
FIG. 7D is a plot of sums and differences of the fundamental and harmonic responses in FIG. 6D centered at a 40 mm depth.
Figure 7E:
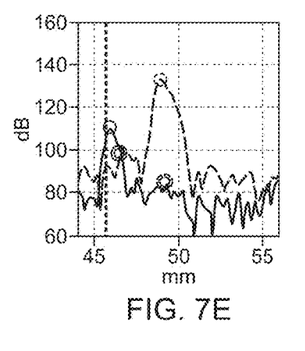
FIG. 7E is a plot of sums and differences of the fundamental and harmonic responses in FIG. 6E centered at a 50 mm depth.
Figure 7F:
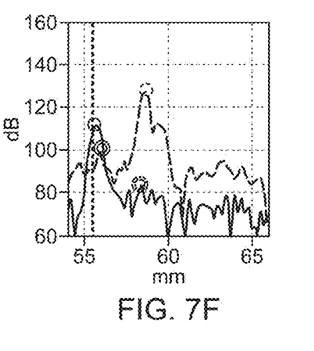
FIG. 7F is a plot of sums and differences of the fundamental and harmonic responses in FIG. 6F centered at a 60 mm depth.

FIGS. 6A-F are intensity plots of fundamental and harmonic responses of a subject region to an exponentially swept ultrasound chirp signal centered at varying depths of the subject region. As shown in FIG. 6C, the fundamental response, e.g. at point 600, is not collocated at a depth of 30 mm with the harmonic response, e.g. at point 602. The same non-collocation of the fundamental and harmonic signals can be seen from the other intensity plots FIGS. 6A, B, D, E, and F with respect to range at the points located at other increments of 10 mm offsets. As such, the exponentially swept ultrasound chirp signal is able to separate in time/distance the harmonic and fundamental responses.

FIGS. 7A-F are plots of sums and differences of the fundamental and harmonic responses shown in FIGS. 6A-F at the varying depths of the subject region. As can be seen from the target at 30 mm the response from the fundamental signal, at point 700, is located at the expected range, while that of the harmonic signal is located closer to the 26 mm range, at point 702. A similar offset in time/range is also observed from the points throughout the entire graph. This clearly demonstrates that not only are the harmonic and fundamental responses separated in time/distance, but also the signal response that is associated with the fundamental and that with the harmonic can also be separated for analysis, in particular for identifying non-linear properties of the subject region.

Figure 8:
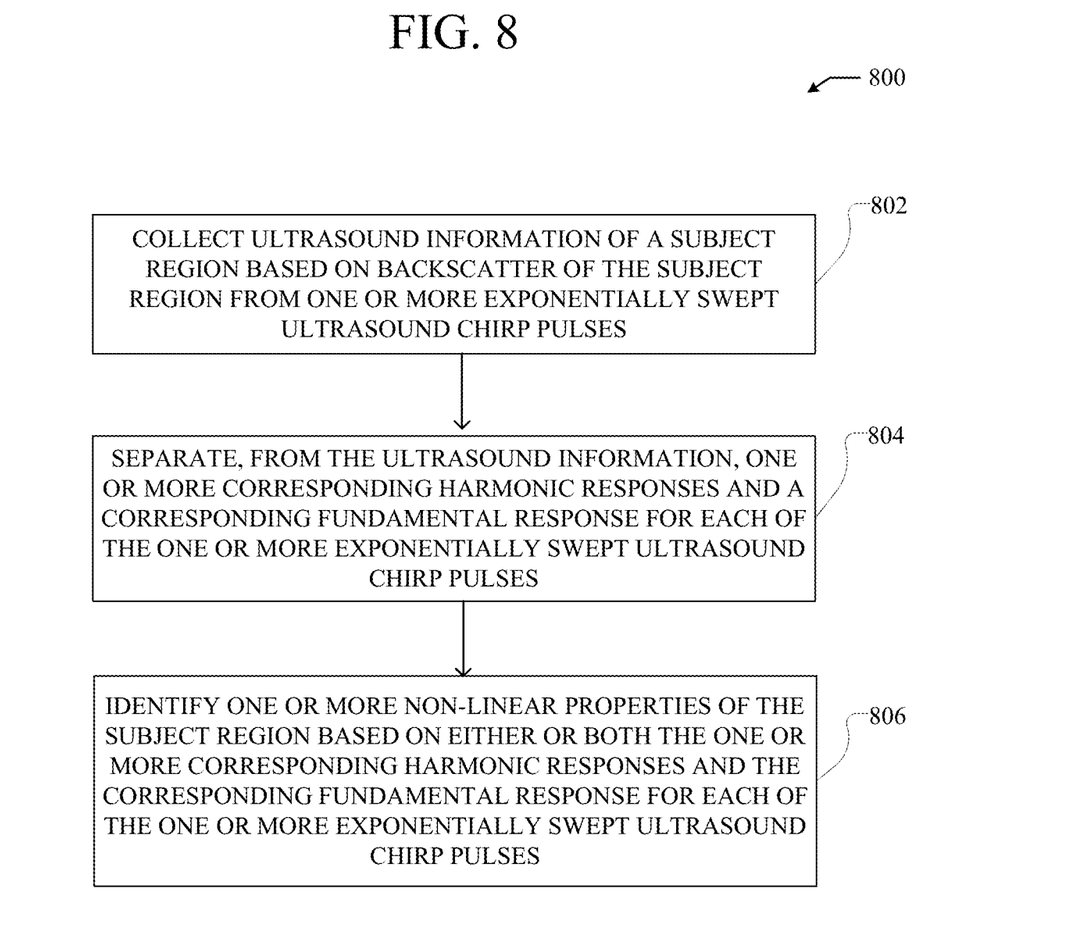
FIG. 8 is a flowchart of an example method for identifying non-linear properties of a subject region through an exponentially swept ultrasound chirp pulse.

FIG. 8 is a flowchart 800 of an example method for identifying non-linear properties of a subject region through an exponentially swept ultrasound chirp pulse. The example method shown in FIG. 8, and other methods and techniques for ultrasound imaging described herein, can be performed by an applicable ultrasound imaging system, such as the ultrasound system 100 shown in FIG. 1. For example, the techniques for ultrasound imaging described herein can be implemented using either or both the ultrasound transducer 110 and the main processing console 118, e.g. the image processor 112, of the ultrasound system 100.

At step 802, ultrasound information of a subject region is collected. The ultrasound information can include ultrasound information of one or more exponentially swept ultrasound chirp purses transmitted towards a subject region. For example, the ultrasound information can include a transmit profile of one or more exponentially swept ultrasound chirp pulses transmitted towards the subject region. Further, the ultrasound information can include backscatter information of both fundamental and harmonic responses generated by the subject region in response to one or more exponentially swept ultrasound chirp pulses transmitted towards the subject region.

As the exponentially swept ultrasound chirp pulse produces time shifted harmonic and fundamental responses, the backscatter information can include information related to the time shifted harmonic and fundamental responses. For example, the ultrasound information can include the harmonic and fundamental responses time shifted with respect to each other as a result of non-linearity in the subject region. In turn, the harmonic and fundamental responses can be analyzed, e.g. based on the time shift, to identify non-linear properties of the subject region.

The ultrasound information can include a plurality of ultrasound images, or otherwise data used to generate the plurality ultrasound images, of the subject region based on the fundamental and harmonic signals. The plurality of ultrasound images of the subject region can be superimposed with respect to each other based on one or more spatial offsets. For example, a feature in the subject region can be displaced by a spatial offset in the plurality of ultrasound images. The one or more spatial offsets can correspond to the fundamental and harmonic signals. Specifically, the one or more spatial offsets can correspond to one or more time delays between the harmonic and fundamental signals. In turn and as will be discussed in greater detail later, the spatial offset(s) in the superimposed ultrasound images can serve as a basis for identifying non-linear properties of the subject region from the ultrasound information.

At step 804, one or more corresponding harmonic responses and a corresponding fundamental response can be separated from the ultrasound information for each of the one or more exponentially swept ultrasound chirp pulses. The corresponding harmonic response(s) and the fundamental response can be separated from each other in the ultrasound information to identify one or more non-linear properties of the subject region. Specifically, the corresponding harmonic response(s) and the fundamental response can be separated from each other to identify a time offset between the harmonic response(s) and the fundamental response. More specifically, the corresponding harmonic response(s) and the fundamental responses can be separated from each other to identify a spatial offset between one or more ultrasound images generated from the harmonic response(s) and the fundamental response.

In turn and at step 806, one or more non-linear properties of the subject region can be identified based on either or both the corresponding harmonic response(s) and the fundamental response for each of the one or more exponentially swept ultrasound chirp pulses. Specifically and as will be discussed in greater detail later, the non-linear properties of the subject region can be identified based on the time offset and/or the spatial offset corresponding to the harmonic response(s) and the fundamental response for each of the applied exponentially swept ultrasound chirp pulses.

The fundamental response and the harmonic response(s) can be filtered from the ultrasound information in order to separate the harmonic response(s) and the fundamental response. Specifically, the fundamental response and the harmonic response(s) can be separately filtered from the ultrasound information to separate the fundamental response and the harmonic response(s). For example, the fundamental response and the harmonic response(s) can be filtered from the ultrasound information based on time, e.g. to separate the fundamental response and the harmonic response(s) based on one or more time delays between the fundamental response and the harmonic response(s).

Additionally, the fundamental response and the harmonic response(s) can be separated by canceling out the fundamental response from the ultrasound information. Specifically, the ultrasound information can be processed to cancel out the fundamental response, effectively isolating the harmonic response(s) in the ultrasound information. In turn, non-linear properties of the subject region can be identified based on the remaining harmonic response(s) and potentially in combination with the fundamental response. The fundamental response can be canceled out from the ultrasound information through an applicable signal processing technique. For example, pulse inversion can be applied to cancel out the fundamental response from the ultrasound information.

The fundamental response and the harmonic response(s) can be correlated with each other from the ultrasound information to generate correlated harmonic and fundamental response information. In turn, the non-linear properties of the subject region can be identified from the correlated harmonic and fundamental response information. The harmonic response(s) and the fundamental response can be correlated with each other based on time offset(s) created between the harmonic response(s) and the fundamental response. The time offset(s), as discussed previously can be created as a result of application of the one or more exponentially swept ultrasound chirp pulses to the subject region when the subject region includes non-linear properties. This time offset(s) can be known, based on the characteristics of the one or more exponentially swept ultrasound chirp pulses, e.g. the start and stop frequencies of the pulses. Accordingly, the non-linear properties of the subject region can be identified based on the known time offset(s).

In identifying the non-linear properties of the subject region based on the fundamental and harmonic response(s), one or more corresponding spatial offsets in the subject region can be identified from the correlated harmonic and fundamental response information. In turn, the non-linear properties of the subject region can be identified from the spatial offsets in the subject region. The spatial offsets can correspond to the time delay between the fundamental and harmonic response(s). Further, the spatial offsets can be represented as spatial offsets in a result of processing the ultrasound information including the fundamental and harmonic response(s). Specifically, the spatial offsets can correspond to a spatial offset, e.g. of features, in a plurality of ultrasound images created based on the fundamental and harmonic response(s).

Further, in identifying the non-linear properties of the subject region based on the fundamental and harmonic response(s), the fundamental and harmonic response(s) can be averaged to generate averaged harmonic and fundamental response information. In turn, the non-linear properties of the subject region can be identified based on the averaged harmonic and fundamental response information. The fundamental and harmonic response(s) can be averaged through an applicable averaging technique applied to the ultrasound information including the harmonic and fundamental responses. For example, coherent data averaging can be applied to the ultrasound information to generate the averaged harmonic and fundamental response information.

The non-linear properties identified based on either or both the fundamental and harmonic response(s) for each exponentially swept ultrasound chirp signal can be identified as part of bulk non-linear property estimates for the subject region. For example, identified estimates of a non-linear property can be averaged across the subject region to identify a bulk non-linear property estimate for the specific non-linear property across the subject region. Further, the non-linear properties can be identified on a sub-region basis for different sub-regions of the subject region. For example, values of a non-linear property can be identified or estimated for different portions of the subject region. As follows, a map of non-linear properties of the subject region can be generated. The map of non-linear properties of the subject region can be generated based on the non-linear properties identified on a sub-region basis for the subject region. For example, a map showing different values of a non-linear property across different sub-regions of the subject region can be generated.

The subject region can be a volume region. Specifically, the subject region can be a volume of tissue, e.g. in-vivo tissue. For example, the subject region can include a volume of fatty liver tissue, Cirrhotic liver tissue, Thyroid cancer tissue, Prostate cancer tissue, or Breast cancer tissue. The non-linear properties can be volume non-linear properties of the volume region. Specifically, non-linear properties for the volume region can be bulk non-linear property estimates for the volume region. The ultrasound information for the volume region can be gathered by an applicable ultrasound system for gathering volume ultrasound information. For example, the ultrasound information for the volume region can be gathered by an ultrasound system that incorporates one or more volumetric-based ultrasound transducers.

Figure 9:
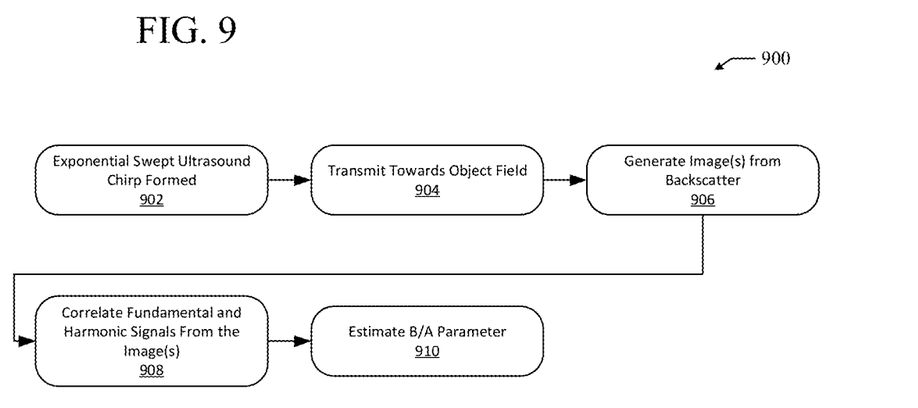
FIG. 9 is a flowchart of an example method for estimating a non-linearity parameter (a B/A parameter) of a subject region through an exponential swept ultrasound chirp signal.

FIG. 9 is a flowchart 900 of an example method for estimating a B/A parameter of a subject region through an exponential swept ultrasound chirp signal. At step 902, an exponential swept ultrasound chirp signal is formed and at step 904 the signal is transmitted towards a subject region. At step 906, the backscatter from the transmit signal is received and processed into one or more images. The desired harmonic signal, typically the second, is then correlated, at step 908, against the fundamental signal, e.g. based on the image(s), to determine the spatial offset in the subject region. At step 910, a B/A parameter for the subject region is estimated based on the correlation between the fundamental and harmonic signals.

The techniques described herein can be applied in an applicable ultrasound imaging mode, such as B-Mode, contrast-enhanced ultrasound ('CEUS'), CD-Mode, 2D/3D/4D, and the like. Specifically, the techniques described herein are not limited to B-Mode but can also be applied to other modes where improved temporal resolution within a region of interest has substantial clinical benefits, such as CEUS.

This disclosure has been made with reference to various exemplary embodiments including the best mode. However, those skilled in the art will recognize that changes and modifications may be made to the exemplary embodiments without departing from the scope of the present disclosure. For example, various operational steps, as well as components for carrying out operational steps, may be implemented in alternate ways depending upon the particular application or in consideration of any number of cost functions associated with the operation of the system, e.g., one or more of the steps may be deleted, modified, or combined with other steps.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

Those having skill in the art will appreciate that many changes may be made to the details of the above-described embodiments without departing from the underlying principles of the invention. The scope of the present invention should, therefore, be determined only by the following claims.

What is claimed is:

1. A method comprising:
    transmitting, via an ultrasound transducer, one or more exponentially swept ultrasound chirp pulses toward a subject region;
    receiving, via the ultrasound transducer, backscatter of the subject region from the one or more exponentially swept ultrasound chirp pulses;
    collecting, using one or more processors, ultrasound information of the subject region from the backscatter;
    separating, using the one or more processors from the ultrasound information, one or more corresponding harmonic responses and a corresponding fundamental response for each of the one or more exponentially swept ultrasound chirp pulses;
    identifying, using the one or more processors, one or more non-linear properties of the subject region based on one or more time offsets between the one or more corresponding harmonic responses and the corresponding fundamental response; and
    generating, using the one or more processors, a map of the one or more non-linear properties of the subject region across the subject region.

2. The method of claim 1, wherein the subject region includes in-vivo tissue.

3. The method of claim 1, wherein the one or more non-linear properties of the subject region include one or more B/A parameters of the subject region.

4. The method of claim 1, further comprising separately filtering the corresponding fundamental response and the one or more corresponding harmonic responses for each of the one or more exponentially swept ultrasound chirp pulses from the backscatter as part of separating the one or more corresponding harmonic responses and the corresponding fundamental response for each of the one or more exponentially swept ultrasound chirp pulses from the ultrasound information.

5. The method of claim 1, further comprising canceling out the corresponding fundamental response for each of the one or more exponentially swept ultrasound chirp pulses from the backscatter to identify the one or more corresponding harmonic responses for each of the one or more exponentially swept ultrasound chirp pulses from the backscatter as part of separating the one or more corresponding harmonic responses and the corresponding fundamental response for each of the one or more exponentially swept ultrasound chirp pulses from the ultrasound information.

6. The method of claim 5, further comprising applying pulse inversion to cancel out the corresponding fundamental response for each of the one or more exponentially swept ultrasound chirp pulses from the backscatter.

7. The method of claim 1, further comprising:
    correlating the one or more corresponding harmonic responses with the corresponding fundamental response for each of the one or more exponentially swept ultrasound chirp pulses to generate correlated harmonic and fundamental response information; and
    identifying the one or more non-linear properties of the subject region based on the correlated harmonic and fundamental response information.

8. The method of claim 7, wherein the one or more corresponding harmonic responses are correlated with the corresponding fundamental response for each of the one or more exponentially swept ultrasound chirp pulses based on a corresponding time offset between each of the one or more corresponding harmonic responses and the corresponding fundamental response for each of the one or more exponentially swept ultrasound chirp pulses.

9. The method of claim 7, wherein each of the one or more time offsets between the one or more corresponding harmonic responses and the corresponding fundamental response corresponds to a respective spatial offset, and the correlated harmonic and fundamental response information includes a plurality of ultrasound images of the subject region superimposed with respect to each other by one or more corresponding spatial offsets, the method further comprising:
    determining the one or more corresponding spatial offsets from the correlated harmonic and fundamental response information; and
    identifying the one or more non-linear properties of the subject region based on the one or more corresponding spatial offsets.

10. The method of claim 1, further comprising:
    applying coherent data averaging between the one or more corresponding harmonic responses and the corresponding fundamental response for each of the one or more exponentially swept ultrasound chirp pulses to generate averaged harmonic and fundamental response information; and
    identifying the one or more non-linear properties of the subject region based on the averaged harmonic and fundamental response information.

11. The method of claim 1, wherein the one or more non-linear properties of the subject region are identified as part of bulk non-linear property estimated for the subject region.

12. The method of claim 1, wherein the subject region is a volume region, the method further comprising identifying the one or more non-linear properties across the volume region.

13. The method of claim 12, wherein the ultrasound information is generated across the volume region by one or more volumetric-based ultrasound transducers.

14. The method of claim 12, wherein the one or more non-linear properties of the subject region are identified as part of bulk non-linear property estimated for the volume region.

15. The method of claim 12, wherein the subject region is a volume of tissue and the one or more non-linear properties are properties of the volume of tissue.

16. The method of claim 15, wherein the volume of tissue includes at least one of fatty liver tissue, Cirrhotic liver tissue, Thyroid cancer tissue, Prostate cancer tissue, and Breast cancer tissue.

17. The method of claim 1, wherein identifying the one or more non-linear properties of the subject region comprises:
   measuring the one or more time offsets between the one or more corresponding harmonic responses and the corresponding fundamental response for each of the one or more exponentially swept ultrasound chirp pulses; and
   comparing the measured one or more time offsets with calculated one or more time offsets to identify the one or more non-linear properties of the subject region.

18. The method of claim 1, wherein generating a map of the one or more non-linear properties of the subject region across the subject region comprises generating a map showing different values of a non-linear property across different sub-regions of the subject region.

19. The method of claim 1, wherein identifying the one or more non-linear properties of the subject region based on the one or more time offsets between the one or more corresponding harmonic responses and the corresponding fundamental response comprises:
   processing, using the one or more processors, the ultrasound information to generate two or more ultrasound images of the subject region superimposed with respect to each other based on at least the one or more time offsets between the one or more corresponding harmonic responses and the corresponding fundamental response; and
   analyzing an amount of displacement between the two or more superimposed ultrasound images to identify the one or more non-linear properties of the subject region.

20. The method of claim 1, wherein the one or more exponentially swept ultrasound chirp pulses are defined by equations:

$$x(t) = e^{j2\pi \frac{f_1}{a}(e^{at}-1)}, \text{ and}$$

$$\theta(f) = A(f \log(f) - f) - (A\log f_1 - T_{start})f,$$

wherein $$a = \frac{\ln\left(\frac{f_1}{f_2}\right)}{T},$$

$$A = \frac{T}{\ln\frac{f_2}{f_1}},$$

$f_1$ is a start frequency of an exponentially swept ultrasound chirp pulse, $f_2$ is a stop frequency of the exponentially swept ultrasound chirp pulse, T is a pulse duration of the exponentially swept ultrasound chirp pulse, and $T_{start}$ is a pulse start time of the exponentially swept ultrasound chirp pulse.

21. A system for performing diagnostic sonography comprising:
   an ultrasound transducer configured to:
      transmit one or more exponentially swept ultrasound chirp pulses toward a subject region; and
      receive backscatter of the subject region from the one or more exponentially swept ultrasound chirp pulses; and
   one or more processors configured to:
      collect, using the one or more processors, ultrasound information of the subject region from the backscatter;
      separate, using the one or more processors from the ultrasound information, one or more corresponding harmonic responses and a corresponding fundamental response for each of the one or more exponentially swept ultrasound chirp pulses;
      identify, using the one or more processors, one or more non-linear properties of the subject region based on one or more time offsets between the one or more corresponding harmonic responses and the corresponding fundamental response; and
      generate, using the one or more processors, a map of the one or more non-linear properties of the subject region across the subject region.

22. A system for performing diagnostic sonography comprising:
   one or more processors; and
   a non-transitory computer-readable medium providing instructions accessible to the one or more processors to cause the one or more processors to perform operations comprising:
   transmitting, via an ultrasound transducer, one or more exponentially swept ultrasound chirp pulses toward a subject region;
   receiving, via the ultrasound transducer, backscatter of the subject region from the one or more exponentially swept ultrasound chirp pulses;
   collecting, using one or more processors, ultrasound information of the subject region from the backscatter;
   separating, using the one or more processors from the ultrasound information, one or more corresponding harmonic responses and a corresponding fundamental response for each of the one or more exponentially swept ultrasound chirp pulses;
   identifying, using the one or more processors, one or more non-linear properties of the subject region based on one or more time offsets between the one or more corresponding harmonic responses and the corresponding fundamental response; and
   generating, using the one or more processors, a map of the one or more non-linear properties of the subject region across the subject region.

* * * * *